(12) United States Patent
Putzien et al.

(10) Patent No.: US 10,059,685 B2
(45) Date of Patent: Aug. 28, 2018

(54) 2-HYDROXYETHYL 2-OXO-1,3-DIOXOLANE-4-CARBOXYLATES, THEIR PREPARATION AND USE

(71) Applicant: Construction Research & Technology, GmbH, Trostberg (DE)

(72) Inventors: Sophie Putzien, Ampfing (DE); Burkhard Walther, Taching am See (DE); Maximilian Kohler, Trostberg (DE)

(73) Assignee: Construction Research & Technology, GmbH, Trostberg (DE)

( * ) Notice: Subject to any disclaimer, the term of this patent is extended or adjusted under 35 U.S.C. 154(b) by 120 days.

(21) Appl. No.: 15/121,098

(22) PCT Filed: Feb. 20, 2015

(86) PCT No.: PCT/EP2015/053569
§ 371 (c)(1),
(2) Date: Aug. 24, 2016

(87) PCT Pub. No.: WO2015/132080
PCT Pub. Date: Sep. 11, 2015

(65) Prior Publication Data
US 2017/0008871 A1    Jan. 12, 2017

(30) Foreign Application Priority Data
Mar. 7, 2014 (EP) ..................... 14158345

(51) Int. Cl.
*C07D 317/38* (2006.01)
*C08G 71/04* (2006.01)

(52) U.S. Cl.
CPC .......... *C07D 317/38* (2013.01); *C08G 71/04* (2013.01)

(58) Field of Classification Search
CPC .................................. C07D 317/38
See application file for complete search history.

(56) References Cited

U.S. PATENT DOCUMENTS

| | | | |
|---|---|---|---|
| 7,968,572 B2 | 6/2011 | Nakai et al. | |
| 8,044,194 B2 | 10/2011 | Dubois et al. | |
| 2010/0063104 A1 | 3/2010 | Nakai et al. | |
| 2010/0317838 A1 | 12/2010 | Dubois et al. | |
| 2011/0313177 A1 | 12/2011 | Mecfel-Marczewski et al. | |
| 2014/0228583 A1 | 8/2014 | Mecfel-Marczewski et al. | |
| 2015/0051365 A1 | 2/2015 | Woelfle et al. | |
| 2015/0353521 A1 | 12/2015 | Wölfle et al. | |

FOREIGN PATENT DOCUMENTS

| | | |
|---|---|---|
| EP | 0 001 088 A1 | 3/1979 |
| EP | 1 932 840 A1 | 6/2008 |
| EP | 1 941 946 A1 | 7/2008 |
| EP | 2 397 474 A1 | 12/2011 |
| JP | 7-285960 A | 10/1995 |
| JP | 2006003433 A | 1/2006 |
| WO | WO 2004/003001 A1 | 1/2004 |
| WO | WO 2007/040208 A1 | 4/2007 |
| WO | WO 2011/157551 A1 | 12/2011 |

(Continued)

OTHER PUBLICATIONS

Lima, et al, "Bioisterism: A Useful Strategy for Molecular Modification and Drug Design", Current Medicinal Chemistry, 2005, vol. 12, pp. 23-49, Bentham Science Publishers, Ltd.
PCT/EP2011/058945—International Search Report, dated Nov. 15, 2011.
PCT/EP2011/058945—International Written Opinion, dated Nov. 15, 2011.
PCT/EP2011/058945—International Preliminary Report on Patentability, dated Jul. 27, 2012.
PCT/EP2012/072589—International Search Report, dated Jan. 4, 2013.
PCT/EP2012/072589—International Written Opinion, dated Jan. 4, 2013.
PCT/EP2012/072589—International Preliminary Report on Patentability, dated Jun. 24, 2014.
PCT/EP2014/051784—International Search Report, dated Mar. 5, 2014.
PCT/EP2014/051784—International Written Opinion, dated Mar. 5, 2014.

(Continued)

*Primary Examiner* — Megan McCulley
(74) *Attorney, Agent, or Firm* — Curatolo Sidoti Co., LPA; Joseph G. Curatolo; Salvatore A. Sidoti

(57) ABSTRACT

2-hydroxyethyl 2-oxo-1,3-dioxolane-4-carboxylates of formula (I):

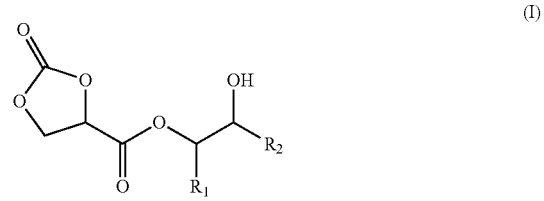

wherein one of $R_1$ and $R_2$ can be hydrogen. $R_1$ and $R_2$, if not hydrogen, and in each case independently of one another, are selected from straight-chain, branched or cyclic $C_{1-22}$-alkyl groups, preferably $C_{1-12}$-alkyl groups, $C_{6-12}$-aryl groups, $C_{6-18}$-aralkyl groups and $C_{6-18}$-alkaryl groups, wherein $R_1$ and/or $R_2$, in each case independently of one another, may comprise at least one additional functional group, selected from hydroxyl groups, ether groups, ester groups, epoxy groups, and double bonds, and wherein $R_2$ may be substituted with up to 10, preferably with 1 to 5, and in particular with 1 or 2 further 2-hydroxyethyl 2-oxo-1,3-dioxolane-4-carboxylic groups. The 2-hydroxyethyl 2-oxo-1,3-dioxolane-4-carboxylates can be prepared by reacting 2-oxo-1,3-dioxolane-4-carboxylic acid with epoxides and can be used for the preparation of hydroxyurethanes through reaction with amines, such as amine hardeners. Moreover, they can also be used as end groups for the blocking of amines.

10 Claims, No Drawings

(56) References Cited

FOREIGN PATENT DOCUMENTS

| WO | WO 2012/065879 A1 | 5/2012 |
|---|---|---|
| WO | WO 2013/092011 A1 | 6/2013 |
| WO | WO 2014/118268 A1 | 8/2014 |

OTHER PUBLICATIONS

Tomita, et al., "Model Reaction for the Synthesis of Polyhydroxyurethanes from Cyclic Carbonates With Amines: Substituent Effect on the Reactivity and Selectivity of Ring-Opening Direction in the Reaction of Five-Membered Cyclic Carbonates with Amine", Journal of Polymer Science, 2001, vol. 39, pp. 3673-3685, John Wiley & Sons Inc.

Lewis, et al., "Synthesis of L-660,631 Methyl Ester and Related Compounds", Tetrahedron Letters, Jan. 1, 1988, vol. 29, No. 19, pp. 2279-2282, Pergamon Press PLC, Great Britain.

Diakoumakos, Constantinos, et al., "Non-Isocyanate-Based Polyurethanes Derived upon the Reaction of Amines with Cyclocarbonate Resins", Macromol. Symp., 2004, vol. 216, pp. 37-46.

Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.

Stevenson, Christian P., et al., "Preparation of (5)-Methyl Glycidate VIA Hydrolytic Kinetic Resolution", Organic Syntheses, 2006, vol. 83, pp. 162-169; Organic Syntheses Collection, 2009, vol. 11, pp. 157-163.

PCT/EP2015/053569—International Search Report, dated Mar. 18, 2015.

PCT/EP2015/053569—International Written Opinion, dated Mar. 18, 2015.

PCT/EP2014/051784—International Preliminary Report on Patentability, dated Aug. 4, 2015.

2-HYDROXYETHYL 2-OXO-1,3-DIOXOLANE-4-CARBOXYLATES, THEIR PREPARATION AND USE

CROSS REFERENCE TO RELATED APPLICATIONS

This application is a national stage application of International Application No. PCT/EP2015/053569, filed 20 Feb. 2015, which claims priority from European Patent Application No. 14158345.0, filed 7 Mar. 2014, which applications are incorporated herein by reference.

The present invention relates to 2-hydroxyethyl 2-oxo-1,3-dioxolane-4-carboxylates of formula (I):

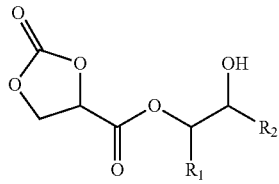
(I)

wherein one of $R_1$ and $R_2$ can be hydrogen. In particular, $R_1$ and $R_2$, if not hydrogen, and in each case independently of one another, are selected from straight-chain, branched or cyclic $C_{1-22}$-alkyl groups, preferably $C_{1-12}$-alkyl groups, $C_{6-12}$-aryl groups, $C_{6-18}$-aralkyl groups and $C_{6-18}$-alkaryl groups, wherein $R_1$ and/or $R_2$, in each case independently of one another, may comprise at least one additional functional group, selected from hydroxyl groups, ether groups, ester groups, epoxy groups, and double bonds, and wherein $R_2$ may be substituted with up to 10, preferably with 1 to 5, and in particular with 1 or 2 further 2-hydroxyethyl 2-oxo-1,3-dioxolane-4-carboxylic groups of formula (Ia):

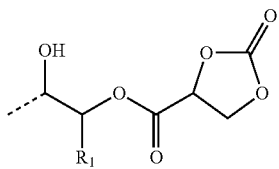
(Ia)

wherein $R_1$ has the above meaning.

Moreover, the present invention relates to a process for the preparation of the 2-hydroxyethyl 2-oxo-1,3-dioxolane-4-carboxylates of the invention by reacting 2-oxo-1,3-dioxolane-4-carboxylic acid of formula (Ib):

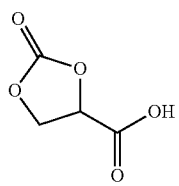
(Ib)

with an epoxide of formula (Ic):

(Ic)

wherein $R_1$ and $R_2$ have the above meanings, to form the 2-hydroxyethyl 2-oxo-1,3-dioxolane-4-carboxylates of formula (I).

Finally, the present invention relates to the use of the 2-hydroxyethyl 2-oxo-1,3-dioxolane-4-carboxylates of the invention for the preparation of hydroxyurethanes and as end groups for the blocking of amines.

Polyurethanes based on polyisocyanates belong to the prior art. These are used for example as adhesives, sealants, casting compositions, as corrosion protection and for coatings. The high resistance to acids, alkalis and chemicals of the cured compositions obtained in this way are advantageous. However, monomeric low molecular weight (poly)isocyanate compounds are toxicologically unacceptable, especially if they are readily volatile or migrate.

Polyurethane systems can also be obtained starting from cyclic carbonate compounds, which are toxicologically acceptable. Thus, e.g. glycerol carbonate (4-(hydroxymethyl)-2-oxo-1,3-dioxolane) is regularly used in cosmetics.

WO 2011/157551 A1 discloses 2-oxo-1,3-dioxolane-4-carboxylic acid and esters thereof according to formula (II):

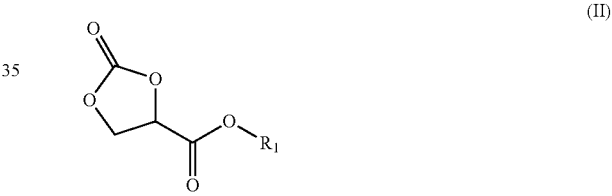
(II)

wherein $R_1$ represents a group selected from straight-chain or branched aliphatic groups, aryl groups, aralkyl groups and alkylaryl groups, and is preferably methyl or ethyl. Moreover, $R_1$ can be an n-valent radical, which may be substituted with at most n−1 further 2-oxo-1,3-dioxolane-4-carboxylic groups of formula (IIa):

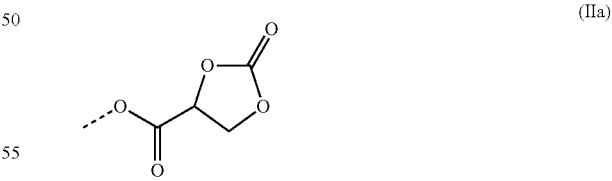
(IIa)

The afore mentioned esters may be cured with amine hardeners to form hydroxyurethanes. However, WO 2011/157551 A1 neither discloses nor suggests the 2-hydroxyethyl 2-oxo-1,3-dioxolane-4-carboxylates of the present invention, nor their preparation and use.

The 2-oxo-1,3-dioxolane-4-carboxylic esters (IIa) of WO 2011/157551 A1 are accessible via transesterification where a low molecular weight 2-oxo-1,3-dioxolane-4-carboxylic acid ester of formula (II) is transesterified with an n-valent polyol, e.g.:

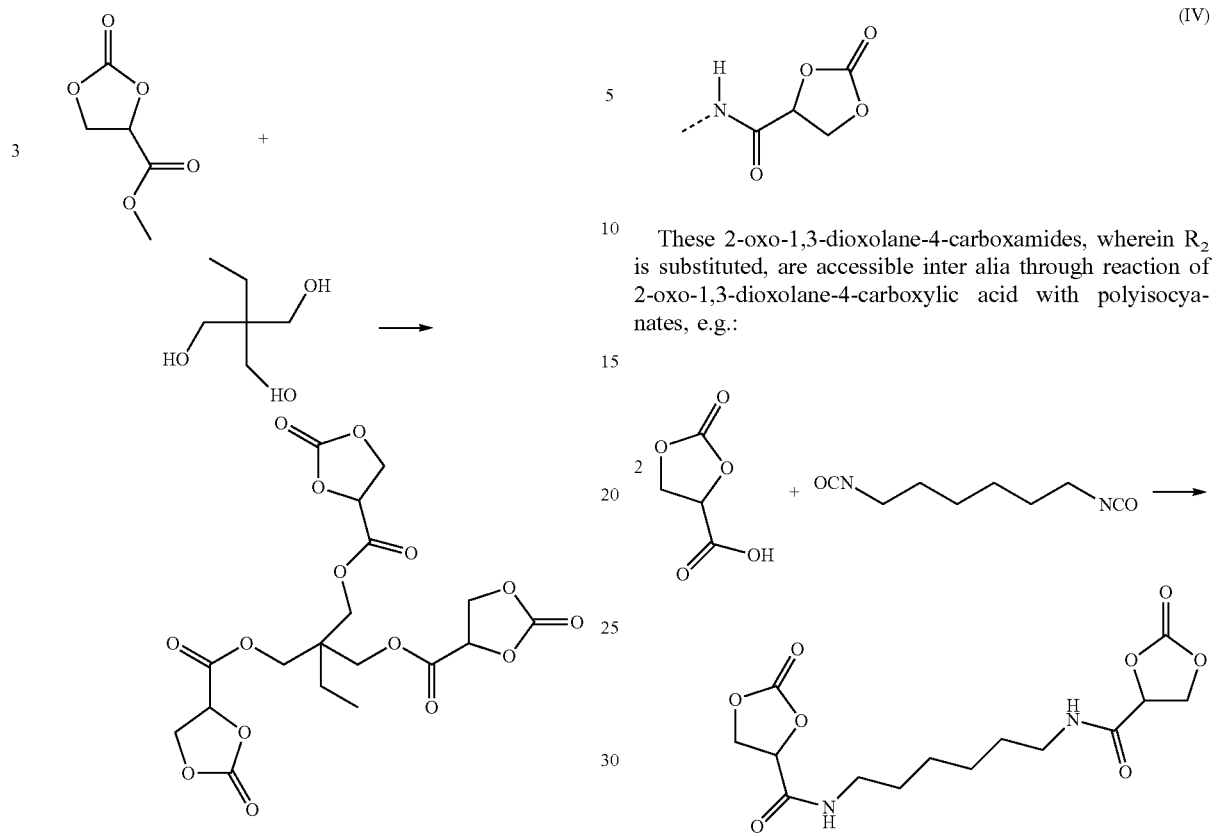

This transesterification reaction is often tedious, requires strong catalysts, and sometimes results in low product yields. Moreover, an expensive low molecular weight 2-oxo-1,3-dioxolane-4-carboxylic acid ester is needed which requires a complicated synthesis (cf. WO 2011/157551 A1, Examples 1-4).

WO 2013/092011 A1 discloses 2-oxo-1,3-dioxolane-4-carboxamides of formula (III):

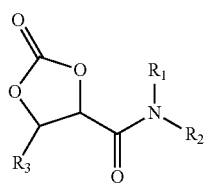

(III)

wherein $R_1$ and $R_2$, in each case independently of one another, are selected from H, straight-chain, branched or cyclic $C_{1-12}$-alkyl groups, $C_{6-10}$-aryl groups, $C_{6-12}$-aralkyl groups and $C_{6-12}$-alkaryl groups or, together with the N atom to which they are bonded, form a 5- to 8-membered ring, and $R_3$ is selected from H and straight-chain, branched or cyclic $C_{1-12}$-alkyl groups, or $R_1$ and $R_3$ are each H, and $R_2$ is an n-valent radical, wherein n is an integer greater than 1, preferably 2-5, in particular 2-3, which is substituted with n−1 further 2-oxo-1,3-dioxolane-4-carboxamide groups of formula (IV):

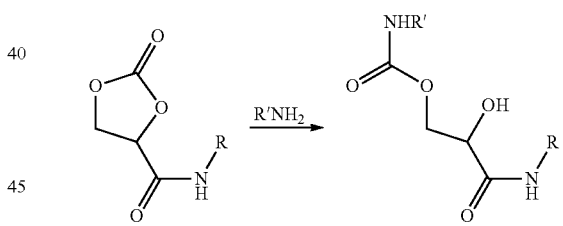

(IV)

These 2-oxo-1,3-dioxolane-4-carboxamides, wherein $R_2$ is substituted, are accessible inter alia through reaction of 2-oxo-1,3-dioxolane-4-carboxylic acid with polyisocyanates, e.g.:

and can also be cured with amine hardeners to form hydroxyurethanes, e.g.:

2-Oxo-1,3-dioxolane-4-carboxylic acid (Ib) is easily accessible through the oxidation of glycerol carbonate (4-(hydroxymethyl)-2-oxo-1,3-dioxolane), which is an industrial product (cf. WO 2013/092011 A1, Examples 6-8). However, the carboxamide-based systems prepared from 2-oxo-1,3-dioxolane-4-carboxylic acid and polyisocyanates often suffer from high viscosity and thus poor workability and require some synthetic efforts and occupational safety and health precautions due to the presence of isocyanates.

It was the object of the present invention to essentially avoid at least some of the disadvantages of the prior art as described above. In general terms, the aim was to provide a 2-oxo-1,3-dioxolane-based system which is toxicologically acceptable, readily accessible, highly reactive with amine hardeners and is suitable as a preferably low-viscous, crosslinkable cyclocarbonate-functional binder. Both, the use of expensive low molecular weight 2-oxo-1,3-dioxolane-4-carboxylic acid esters as starting materials and working with polyisocyanates should be avoided.

These objects have been achieved with the features of the independent claims. The dependent claims relate to preferred embodiments.

It was surprisingly found that suitable crosslinkable cyclocarbonate-functional binders can be prepared in a ring-opening reaction between an epoxide and 2-oxo-1,3-dioxolane-4-carboxylic acid of formula (Ib) (so called "CYCA"). With this approach every epoxide (resin) can be easily converted into a 2-hydroxyethyl cyclocarbonate (resin). The resulting binders bear chemically stable 2-hydroxyethyl carboxylate groups and are often low-viscous. Moreover, due to the presence of the 2-hydroxyethyl group(s), they are also quite hydrophilic and thus compatible with mineral substrates and can be cured with amines to give hydroxypolyurethanes with good chemical and mechanical properties.

It is thus a first subject matter of the present invention to provide 2-hydroxyethyl 2-oxo-1,3-dioxolane-4-carboxylates of formula (I):

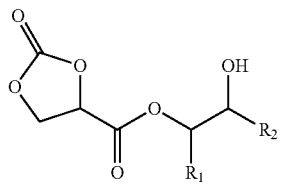

(I)

wherein one of $R_1$ and $R_2$ can be hydrogen.

In particular, $R_1$ and $R_2$, if not hydrogen, and in each case independently of one another, are selected from straight-chain, branched or cyclic $C_{1-22}$-alkyl groups, preferably $C_{1-12}$-alkyl groups, $C_{6-12}$-aryl groups, $C_{6-18}$-aralkyl groups and $C_{6-18}$-alkaryl groups, wherein $R_1$ and/or $R_2$, in each case independently of one another, may comprise at least one additional functional group, selected from hydroxyl groups, ether groups, ester groups, epoxy groups, and double bonds, and wherein $R_2$ may be substituted with up to 10, preferably with 1 to 5, and in particular with 1 or 2 further 2-hydroxyethyl 2-oxo-1,3-dioxolane-4-carboxylic groups of formula (Ia):

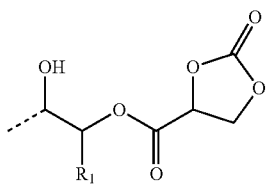

(Ia)

wherein $R_1$ has the above meaning.

Preferred meanings of $R_1$ and/or $R_2$ are e.g. methyl, ethyl, n-propyl, iso-propyl, n-butyl, sec-butyl, tert-butyl, n-pentyl, neo-pentyl, n-hexyl, 2-ethyl-n-hexyl, cyclohexyl, phenyl, benzyl, polyether groups (such as $C_{2-5}$-(poly)oxyalkylene groups), polycarbonate groups, polyester groups, saturated and unsaturated fatty acid ester groups, poly-(meth)acrylate groups, and combinations thereof.

A preferred embodiment of the 2-hydroxyethyl 2-oxo-1,3-dioxolane-4-carboxylates of the invention is a 2-hydroxyethyl 2-oxo-1,3-dioxolane-4-carboxylate, comprising a glycerol ester moiety:

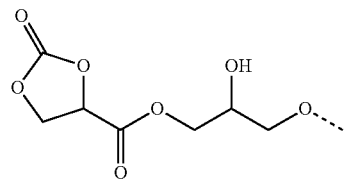

(Id)

A second subject matter of the present invention is to provide a process for the preparation of the 2-hydroxyethyl 2-oxo-1,3-dioxolane-4-carboxylates of the invention by reacting 2-oxo-1,3-dioxolane-4-carboxylic acid of formula (Ib):

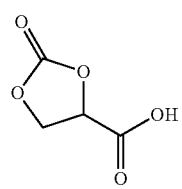

(Ib)

with an epoxide of formula (Ic):

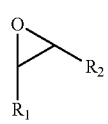

(Ic)

wherein $R_1$ and $R_2$ have the above meanings, to give the 2-hydroxyethyl 2-oxo-1,3-dioxolane-4-carboxylates of formula (I). It is obvious that $R_1$ and $R_2$ can be interchanged in the final product of formula (I) because the epoxide ring may be attacked from either side, but for clarity of definition reasons it will be adhered to the notation as shown in formula (I).

Said process may suitably be carried out in the presence of a catalyst selected from tertiary amines, organometallic compounds such as chromium compounds, and mixtures thereof.

A further subject matter of the present invention is the use of the 2-hydroxyethyl 2-oxo-1,3-dioxolane-4-carboxylates of the invention for the preparation of hydroxyurethanes through reaction with amines, such as amine hardeners.

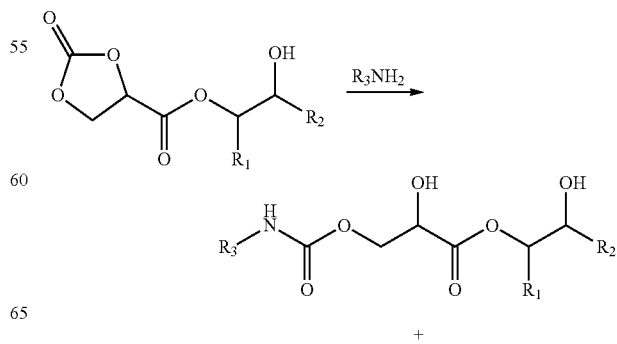

+

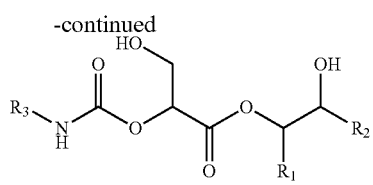

Here in principle two different hydroxyurethanes are possible, namely hydroxyurethanes with primary or secondary hydroxyl groups. In this respect, it has been shown that the electron-withdrawing COO group diverts the reaction essentially in the direction of the hydroxyurethanes with secondary hydroxyl groups since, in the event of attack of the nucleophilic nitrogen atom, the negative charge on the oxygen atom which is closer to the COO group is better stabilized. Hydroxyurethanes with secondary hydroxyl groups have the additional advantage that the back-reaction is hindered. Theoretically, an attack of the amine at the ester group would also be conceivable; however, it was shown analytically that in the present case the amine essentially attacks only the 2-oxo-1,3-dioxolane group.

Suitable amines are primary and secondary amines with alkyl groups, aryl groups, aralkyl groups, and alkylaryl groups. Primary amines react much quicker than secondary amines; aliphatic amines react more quickly than aromatic amines. As regards the relative reactivities of different amines, compare C. Diakoumakos, D. Kotzev, Non-Isocyanate-Based Polyurethanes Derived upon the Reaction of Amines with Cyclocarbonate Resins, Macromol. Symp., 216, 37-46 (2004), in particular scheme 4 on p. 45. All of the amines specified therein and standard amine hardeners that are known to a person skilled in the art are suitable for carrying out the present invention. Relatively high molecular weight amines such as e.g. Jeffamine® from Huntsman Corp. and polyether amines from BASF SE are also suitable.

One advantage of the 2-hydroxyethyl 2-oxo-1,3-dioxolane-4-carboxylates (I) of the invention lies in the relatively high hydrophilicity of these systems, which can be attributed to the OH groups present. These OH groups are in principle also available for the crosslinking with polyisocyanates, although the isocyanate-free systems possible according to the invention are preferred on account of their lower toxicity.

The hydrophilicity of these novel molecules can be expressed, for instance, in terms of their HLB values ("HLB" being the hydrophilic/lipophilic balance):

$$HLB = 20 * M_{hy}/M$$

wherein
$M_{hy}$=molecular weight of the hydrophilic portion(s)
$M$=molecular weight of the whole molecule.

HLB values below 10 indicate lipophilic substances, HLB values over 10 indicate hydrophilic substances. Higher HLB values indicate higher hydrophilic character.

When comparing, for instance, the tri-substituted reaction product of Example 7 or 10 of WO 2011/157551 A1:

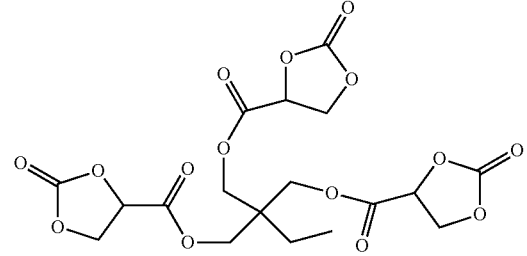 [SMILES: CCC(COC(=O)C1COC(=O)O1)(COC(=O)C1COC(=O)O1)COC(=O)C1COC(=O)O1]

with the tri-substituted reaction product of Example 2 hereinbelow:

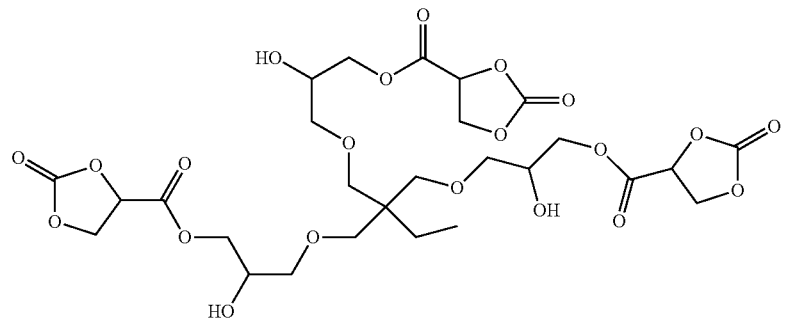 [SMILES: CCC(COCC(O)COC(=O)C1COC(=O)O1)(COCC(O)COC(=O)C1COC(=O)O1)COCC(O)COC(=O)C1COC(=O)O1]

the former molecule has an HLB value of 16.5 while the latter one has an HLB value of 17.6 (assuming that the entire glycerol ester moiety is hydrophilic).

Moreover, when producing polyhydroxyurethane systems which are based on the 2-hydroxyethyl 2-oxo-1,3-dioxolane-4-carboxylates of the invention, bubble formation as a result of formed $CO_2$ may not arise, even in the presence of moisture. Consequently, largely pore- and bubble-free coatings are possible, which is sometimes problematic for classic polyurethane systems. Furthermore, the thermal stability of such polyhydroxyurethane systems is also higher than the stability of classic polyurethane systems.

Moreover, the title compounds of formula (I) can be used to block amines (so-called "end caps"), which constitutes a further subject matter of the present invention. This is also of interest with regard to conventional, amine-crosslinked polyurethane systems since an amine excess can lead to discolorations, while an isocyanate excess is toxicologically unacceptable.

The present invention is now illustrated in more detail by reference to the examples hereinbelow.

EXAMPLES

Example 1: Reaction of CYCA with Phenyl Glycidyl Ether

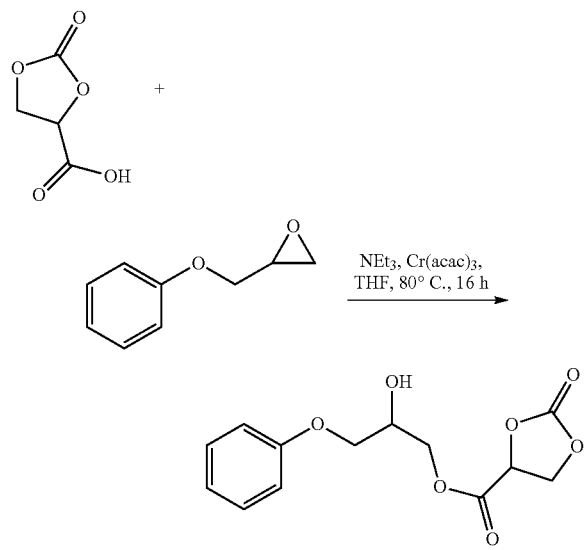

A cyclocarbonate-functional molecule can be prepared from phenyl glycidyl ether with 2-oxo-1,3-dioxolane-4-carboxylic acid ("CYCA") in the presence of a chromium catalyst.

2.85 g phenyl glycidyl ether (0.019 mol), 2.50 g 2-oxo-1,3-dioxolane-4-carboxylic acid (0.019 mol), 0.0025 g triethylamine and 0.017 g chromium (III) acetyl acetonate (Cr(acac)$_3$) were dissolved in 20 ml of dry THF and stirred at 80° C. for 16 h. After evaporation of the solvent, the product was obtained as slightly purple liquid in quantitative yield.

$^1$H-NMR (CDCl$_3$): 7.28 (m, 2H, Ar), 7.96 (m, 1H, Ar), 6.88 (m, 2H, Ar), 5.07 (m, 1H, cyclocarbonate), 4.64 (m, 1H, cyclocarbonate), 4.43 (m, 1H, cyclocarbonate), 4.24-3.33 (m, 6H, CH, CH$_2$O and OH) ppm.

IR (v, cm$^{-1}$): 3485 (bw), 2927 (w), 2876 (w), 1791 (s, cyclocarbonate), 1747 (s), 1599 (m), 1493 (m), 1387 (m), 1293 (w), 1235 (s), 1154 (s), 1093 (s), 888 (w), 814 (m), 755 (s), 699 (s), 509 (m).

Example 2: Reaction of CYCA with Polypox® R 20

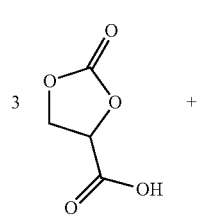

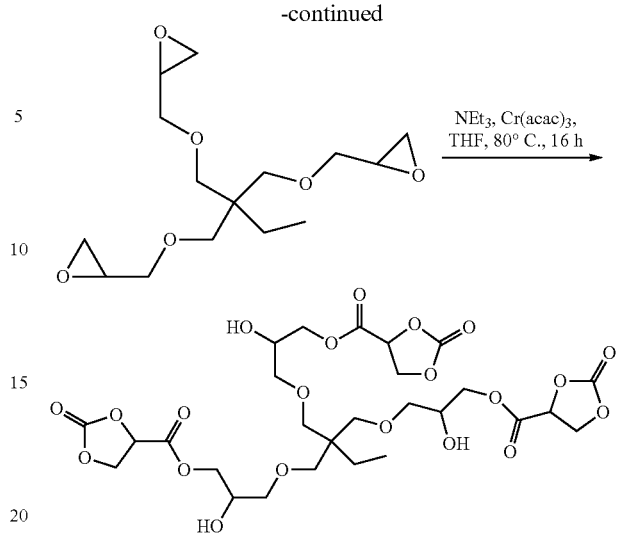

A cyclocarbonate-functional binder can be prepared from Polypox® R 20 (trimethylol-propane-triglycidyl ether, DOW CHEMICAL) with 2-oxo-1,3-dioxolane-4-carboxylic acid in the presence of a chromium catalyst.

Under an atmosphere of dry nitrogen, 30.0 g Polypox® R 20 (0.21 mol epoxide), 27.73 g 2-oxo-1,3-dioxolane-4-carboxylic acid (0.21 mol), 0.062 g triethylamine and 0.098 g chromium (III) acetyl acetonate (Cr(acac)$_3$) were dissolved in 100 ml of dry THF and stirred at 80° C. for 16 h. After evaporation of the solvent, the product was obtained as slightly purple oil in quantitative yield.

$^1$H-NMR (CDCl$_3$): 5.10 (m, 3H, cyclocarbonate), 4.68 (m, 3H, cyclocarbonate), 4.45 (m, 3H, cyclocarbonate), 4.28-3.31 (m, 24H, CH, CH$_2$O and OH), 1.36 (m, 2H, CH$_2$-Ethyl), 0.83 (t, 3H, CH$_3$-Ethyl) ppm.

IR (v, cm$^{-1}$): 3467 (bw), 2924 (m), 2870 (m), 1814 (s, cyclocarbonate), 1746 (s), 1481 (w), 1386 (m), 1225 (m), 1151 (s), 1090 (s), 1060 (s), 945 (m), 851 (w), 767 (m).

Example 3: Reaction of CYCA with Polypox R® 18

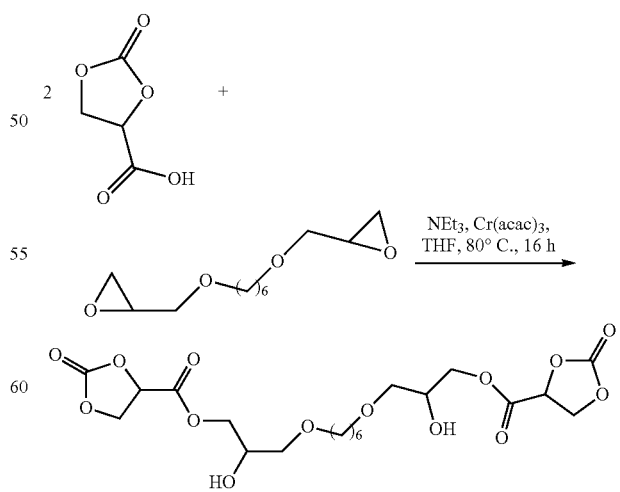

A cyclocarbonate-functional binder can also be prepared from Polypox® R 18 (1,6-hexandiol-diglycidyl ether, DOW CHEMICAL) with 2-oxo-1,3-dioxolane-4-carboxylic acid in the presence of a chromium catalyst, following the same procedure as described in Example 1. The product is obtained as clear oil in quantitative yield.

IR (v, cm$^{-1}$): 3462 (bw), 2934 (m), 2864 (m), 1813 (s, cyclocarbonate), 1794 (s), 1745 (s), 1638 (w), 1538 (w), 1480 (w), 1461 (w), 1386 (m), 1224 (m), 1152 (s), 1090 (s), 1060 (s), 946 (m), 767 (m), 732 (w), 637 (w).

Example 4: Reaction of CYCA with Epoxidized Soybean Oil ("ESO")

A cyclocarbonate-functional binder can also be prepared from epoxidized soy bean oil (ESO 260 from Mythen with idealized formula hereinabove, Meq: 242 g/mol) with 2-oxo-1,3-dioxolane-4-carboxylic acid in the presence of a chromium catalyst, following the same procedure as described in Example 1. The product is obtained as slightly turbid purple oil in quantitative yield.

IR (v, cm$^{-1}$): 3505 (bw), 2925 (m), 2855 (m), 1819 (s, cyclocarbonate), 1738 (s), 1463 (w), 1382 (w), 1224 (m), 1152 (s), 1093 (s), 1061 (s), 767 (m), 727 (w).

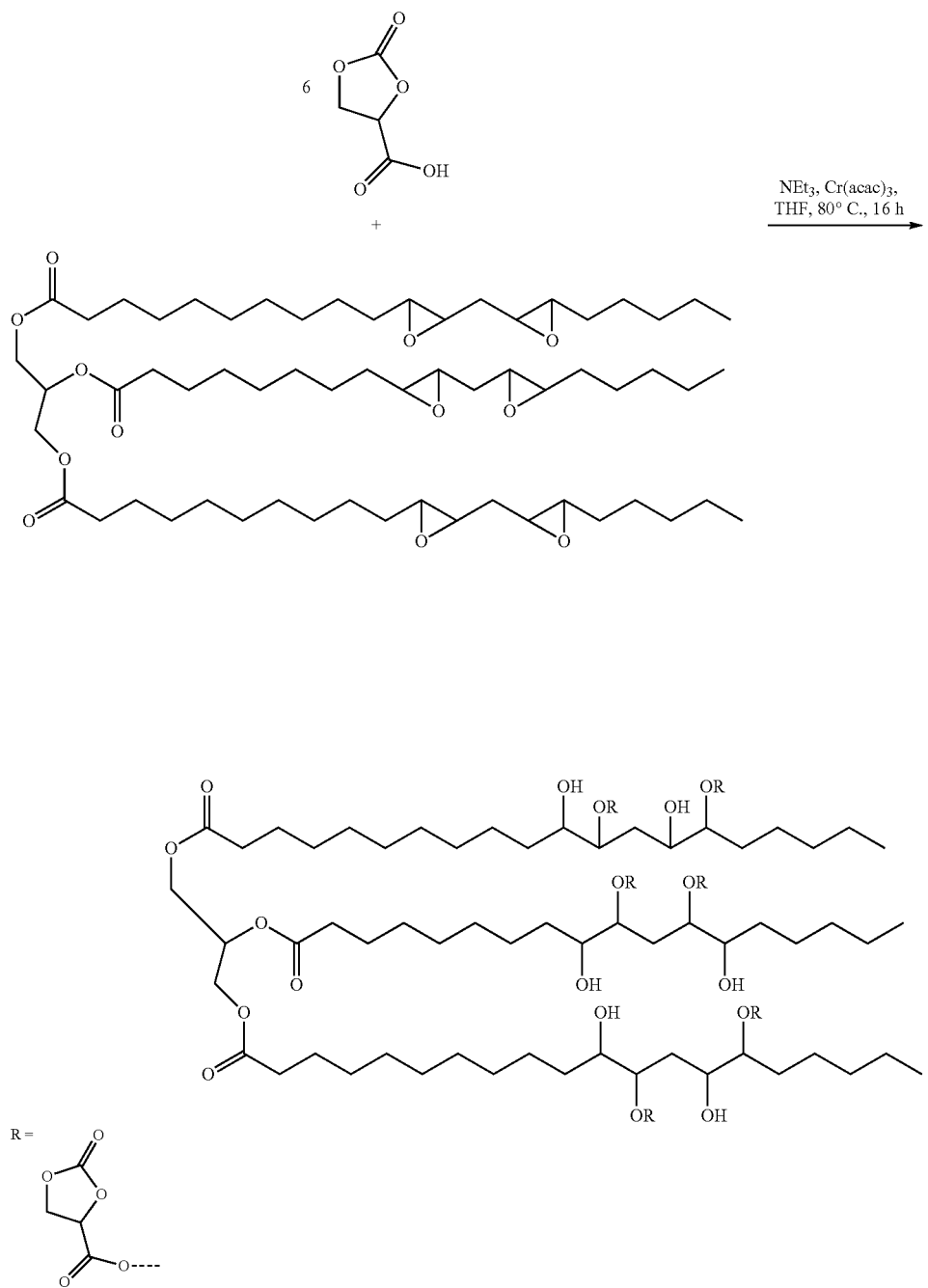

Example 5: Reaction of CYCA with a Bisphenol a Epoxy Resin

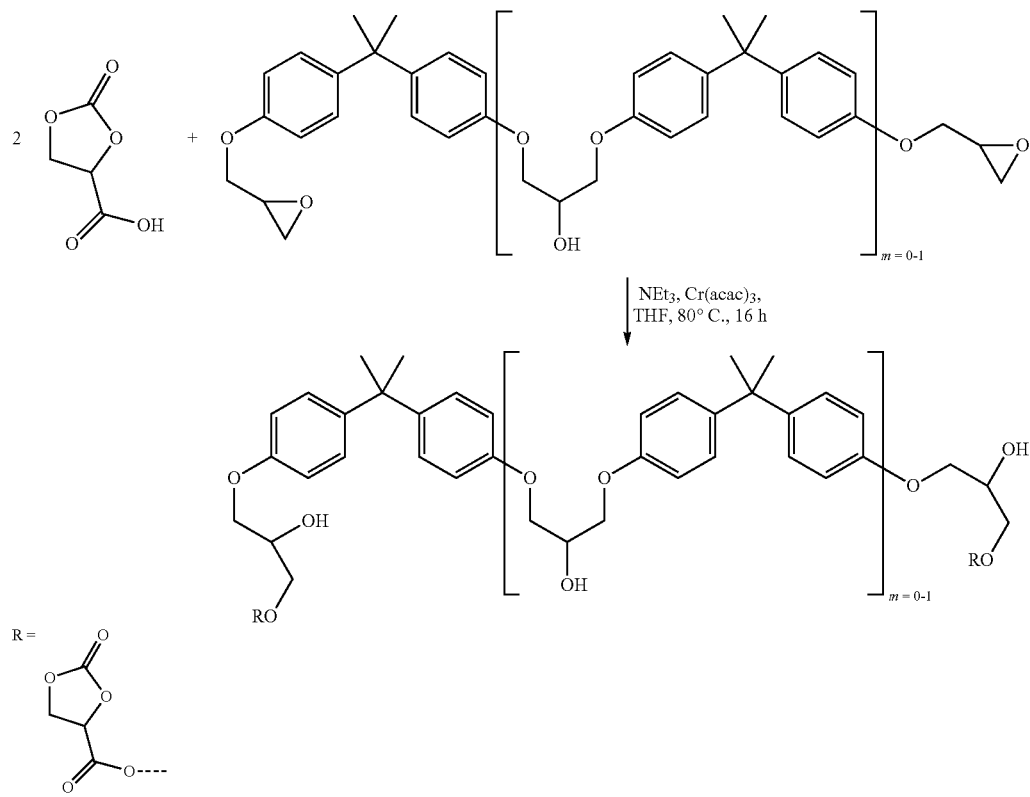

A cyclocarbonate-functional binder can also be prepared from a low-molecular Bisphenol A epoxy resin (i.e. "poly(bisphenol A-co-epichlorohydrin), glycidyl end-capped"; Mn: 377 g/mol, Sigma Alrich) with 2-oxo-1,3-dioxolane-4-carboxylic acid in the presence of a chromium catalyst, following the same procedure as described in Example 1. The product is obtained as slightly turbid purple oil in quantitative yield.

IR (v, cm$^{-1}$): 3495 (bw), 2964 (m), 2933 (m), 1816 (s, cyclocarbonate), 1746 (s), 1607 (m), 1508 (s), 1461 (m), 1384 (w), 1362 (w), 1295 (m), 1224 (m), 1229 (s), 1152 (s), 1093 (s), 1060 (s), 1033 (s), 943 (w), 829 (s), 766 (m), 736 (m), 558 (m).

Example 6: Curing

All thus obtained cyclic carbonate binders can be cured with commercially available amine hardeners such as IPDA or polyetheramines to give polyhydroxyurethanes.

| Reaction | Amount [mol] | Amount [g] | Curing |
|---|---|---|---|
| Polypox® R 20-CYCA | 0.045 | 12.470 | Cured, tacky. |
| IPDA | 0.045 | 3.825 | |
| Polypox® R 20-CYCA | 0.045 | 12.470 | Increase in viscosity, no complete curing, very tacky, foaming. |
| Polyetheramine T 403 | 0.045 | 6.602 | |
| ESO 260-CYCA | 0.01 | 3.745 | Cured, almost tack-free, clumpy, brittle. |
| Lupasol® FG | 0.01 | 0.990 | |
| ESO 260-CYCA | 0.01 | 3.745 | Increase in viscosity but |
| Polyetheramine T 403 | 0.01 | 1.467 | no complete curing, very tacky, foaming. |

The invention claimed is:

1. 2-Hydroxyethyl 2-oxo-1,3-dioxolane-4-carboxylate of formula (I)

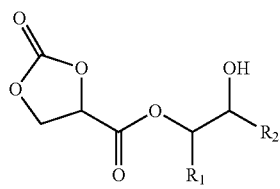

(I)

wherein one of R$_1$ and R$_2$ is optionally hydrogen, wherein R$_1$ and R$_2$, if not hydrogen, in each case independently of one another, are selected from straight-chain, branched or cyclic C$_{1-22}$-alkyl groups, C$_{6-12}$-aryl groups, C$_{6-18}$-aralkyl groups and C$_{6-18}$-alkaryl groups, wherein R$_1$ and/or R$_2$, in each case independently of one another, may comprise at least one additional functional group, selected from hydroxyl groups, ether groups, ester groups, epoxy groups, and double bonds, and wherein $R_2$ is optionally substituted with up to 10 further 2-hydroxyethyl 2-oxo-1,3-dioxolane-4-carboxylic groups of formula (1a)

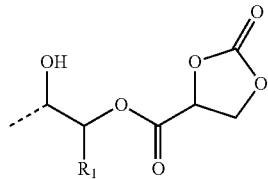

(1a)

wherein $R_1$ has the meaning given.

2. The 2-Hydroxyethyl 2-oxo-1,3-dioxolane-4-carboxylate of claim 1, wherein $R_1$ and $R_2$, in each case independently of one another, are selected from methyl, ethyl, n-propyl, iso-propyl, n-butyl, sec-butyl, tert-butyl, n-pentyl, neo-pentyl, nhexyl, 2-ethyl-n-hexyl, cyclohexyl, phenyl, benzyl, polyether groups, polycarbonate groups, polyester groups, fatty acid ester groups, poly(meth)acrylate groups, and combinations thereof.

3. The 2-Hydroxyethyl 2-oxo-1,3-dioxolane-4-carboxylate of claim 1, comprising the glycerol ester moiety:

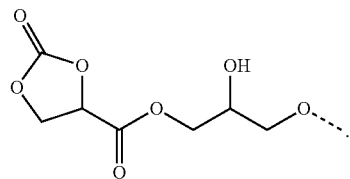

(Id)

4. A process for the preparation of 2-hydroxyethyl 2-oxo-1,3-dioxolane-4-carboxylates as defined in claim 1, characterized in that 2-oxo-1,3-dioxolane-4-carboxylic acid of formula (1b)

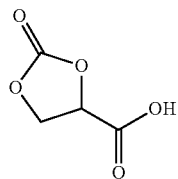

(Ib)

is reacted with an epoxide of formula (1c)

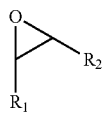

(Ic)

wherein $R_1$ and $R_2$ have the meanings given, to give the 2-hydroxyethyl 2-oxo-1,3-dioxolane-4-carboxylate of formula (I).

5. The process of claim 4, which is carried out in the presence of a catalyst selected from tertiary amines, organometallic compounds, and mixtures thereof.

6. The 2-Hydroxyethyl 2-oxo-1,3-dioxolane-4-carboxylate of claim 1, wherein $R_1$ and $R_2$, if not hydrogen, in each case independently of one another, are selected from straight-chain, branched or cyclic $C_{1-12}$-alkyl groups.

7. The 2-Hydroxyethyl 2-oxo-1,3-dioxolane-4-carboxylate of claim 1, wherein $R_2$ is substituted with 1 to 5 further 2-hydroxyethyl 2-oxo-1,3-dioxolane-4-carboxylic groups of formula (1a).

8. The 2-Hydroxyethyl 2-oxo-1,3-dioxolane-4-carboxylate of claim 1, wherein $R_2$ is substituted with 1 or 2 further 2-hydroxyethyl 2-oxo-1,3-dioxolane-4-carboxylic groups of formula (1a).

9. A process comprising reacting the 2-hydroxyethyl 2-oxo-1,3-dioxolane-4-carboxylate as defined in claim 1 with an amine to form a hydroxyurethane.

10. A process comprising blocking an amine with the 2-hydroxyethyl 2-oxo-1,3-dioxolane-4-carboxylate as defined in claim 1 as an end group.

* * * * *